United States Patent [19]

Shackleton et al.

[11] 3,960,948

[45] June 1, 1976

[54] SUBSTITUTED CHLOROACYLANILIDES

[75] Inventors: Frank Shackleton, Rochdale; Donald Butler, Salford, both of England

[73] Assignee: Lankro Chemicals Group Limited, England

[22] Filed: Feb. 10, 1975

[21] Appl. No.: 548,577

[30] Foreign Application Priority Data
Feb. 14, 1974   United Kingdom.................. 6701/74

[52] U.S. Cl............................................ 260/562 B
[51] Int. Cl.².......................................... C07C 103/32
[58] Field of Search ................................ 260/562 B

[56] References Cited
FOREIGN PATENTS OR APPLICATIONS
1,245,958    8/1967    Germany

*Primary Examiner*—C. Davis
*Attorney, Agent, or Firm*—Bacon & Thomas

[57] ABSTRACT

The invention concerns a process for the preparation of substituted chloroacylanilides of the general formula:

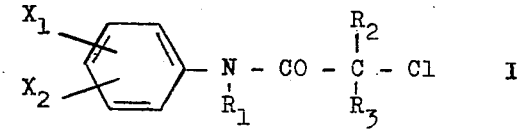

wherein $R_1$ represents an alkyl group having from 1 to 4 carbon atoms or a phenyl group; $R_2$ represents a hydrogen atom or halogen atom; $R_3$ represents a hydrogen atom or an alkyl group having from 1 to 4 carbon atoms and $X_1$ and $X_2$, which may be the same or different, represent a hydrogen atom, a halogen atom, a methyl group or an ethyl group. The process comprises acylating a substituted aniline of the general formula:

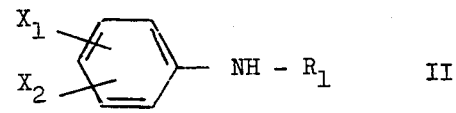

wherein $R_1$, $X_1$ and $X_2$ are as above defined, in the presence of phosphoryl chloride under substantially anhydrous conditions with a chlorocarboxylic acid of the general formula:

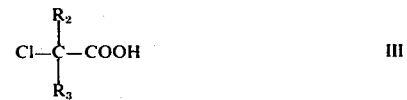

wherein $R_2$ and $R_3$ are as above defined.

Particularly suitable compounds of general Formula II are N-methyl aniline and N-isopropyl aniline, and particularly suitable compounds of general Formula III are chloroacetic acid, dichloroacetic acid and α-chloropropionic acid and α-chlorobutyric acid. The compounds of general Formula I have phytotoxic effects and some are active herbicides.

9 Claims, No Drawings

SUBSTITUTED CHLOROACYLANILIDES

The present invention relates to processes for the preparation of substituted chloroacyl anilides, and in particular to a novel process for the preparation of substituted chloroacyl anilides of the general formula I:

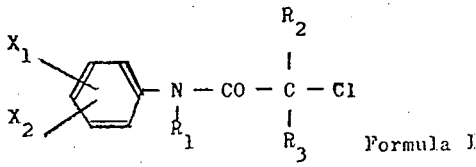

Formula I wherein $R_1$ represents an alkyl group having from 1 to 4 carbon atoms or a phenyl group; $R_2$ represents a hydrogen atom or a halogen atom; $R_3$ represents a hydrogen atom or an alkyl group having from 1 to 4 carbon atoms; $X_1$ and $X_2$ each individually represent a hydrogen atom, a halogen atom, a methyl group or an ethyl group.

N-substituted halogen acyl anilides of the general formula I have phytotoxic effects and some are known to be active herbicides. U.S. Pat. No. 2,863,752 describes the production of certain N-substituted halogen acyl anilides by the reaction of an acyl halide with the required substituted aniline. In this process, the acid chloride (usually a chloroacetyl chloride) is prepared in a first reaction step. The acid chloride is then reacted with the required substituted aniline in an organic solvent in the presence of an alkaline substance and water, at a temperature below 0°C. After completion of the reaction, the product is extracted, the solvent is distilled off and the product is purified by crystallisation.

British Patent Specification No. 1,316,782 describes a single stage process for the preparation of substituted halogen acyl anilides in which these compounds are prepared directly by the reaction of the chlorocarboxylic acid and the appropriately substituted aniline in the presence of phosphorus trichloride at a temperature of about 100°C. After removal of the excess phosphorus trichloride by distillation and washing with water, a product suitable for use in herbicides is obtained.

The process described in British Patent Specification No. 1,316,782 has certain technical and commercial advantages over the prior processes. One of the main advantages advanced for the processes of this specification is that the chlorocarboxylic acid (mono or di-chloro acetic acids, α-chloro-propionic acid, α-chlorobutyric acid etc.) are cheaper and more readily available than the corresponding acid chlorides to be obtained from them. In particular, chloroacetyl cloride is a rather noxious material, having high vapour pressure, being highly toxic and hydrolysing rapidly in a humid atmosphere with resultant corrosive effects. The alternative use of chloroacetic acid anhydride has similar complications.

As British Patent Specification No. 1,316,782 points out, phosphorus trichloride is a cheap, readily available material, and the chlorocarboxylic acids used are either liquids at room temperature or low melting solids, so that their handling is relatively convenient.

Surprisingly, it has now been found that the substituted halogen acyl anilides can be prepared directly from the chlorocarboxylic acid and the appropriately substituted aniline by reaction in the presence of phosphoryl chloride ($POCl_3$). Chloroacyl anilides are obtained in a higher yield and in a higher state of purity than are obtained in the process described in British Patent Specification No. 1,316,782. It has been found that the improvements obtained are relatively much greater when the amine to be reacted is technical material such as is commonly available commercially. The process of the present invention therefore avoids the elaborate purification steps which are otherwise necessary in preparing the amine.

Accordingly, the present invention provides a process for the preparation of substituted chloracyl anilides of the general formula:

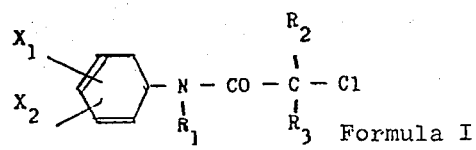

Formula I wherein $R_1$ represents an alkyl group having from 1 to 4 carbon atoms or a phenyl group; $R_2$ represents a hydrogen atom or halogen atom; $R_3$ represents a hydrogen atom or an alkyl group having from 1 to 4 carbon atoms and $X_1$ and $X_2$, which may be the same or different, represent a hydrogen atom, a halogen atom, a methyl group or an ethyl group, which process comprises acylating a substituted aniline of the general formula:

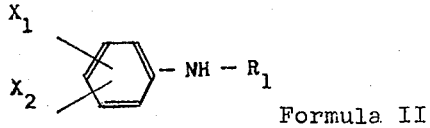

Formula II wherein $R_1$, $X_1$ and $X_2$ are as above defined in the presence of phosphoryl chloride under substantially anhydrous conditions with a chlorocarboxylic acid of the general formula:

Formula III wherein $R_2$ and $R_3$ are as above defined.

Preferred chloroacyl anilides are those derived from N-methyl aniline and N-isopropyl aniline.

Preferred chlorocarboxylic acids are chloroacetic acid, dichloroacetic acid, α-chloropropionic acid and α-chlorobutyric acid.

The reaction is preferably conducted at atmospheric pressure and at a temperature of from 40° to 160° and more preferably at a temperature between 60° and 120°C. The temperature in itself is not too important, provided that it is higher than the solidification point of the reaction intermediates and below the boiling point of the reactants.

Preferably the phosphoryl chloride and the appropriate amine are added to the chlorocarboxylic acid slowly, either continuously or as discrete additions, so that neither of the added materials is in substantial excess for a long period of time. After completion of the reaction the product is preferably purified by pouring the reaction mixture into water, at a temperature above the melting point of the product, cooling sufficiently to allow the product to crystallise, and then cooling to a temperature of from 30° to 35°C. In one preferred form of the process of the invention the precipitated crystallised product is separated from the aqueous phase by filtration, decantation or centrifugation and is then washed with water. After drying, the product is generally suitable for use in herbicidal compositions.

Alternatively the mixture of the crude product may be purified above its melting point by first washing with water and then with dilute caustic soda solution, then distilling to dry and recover unreacted amines. The resultant molten product can then be flaked.

The substituted aniline of Formula II is usually obtained by reacting a substituted aniline of the general formula:

Formula IV wherein $X_1$ and $X_2$ are as defined above with an alkyl chloride or bromide of the formula $R_1Cl$ or $R_1Br$ wherein $R_1$ has the meaning given above. In addition to the desired amine of formula II, the disubtituted amine of the general formula:

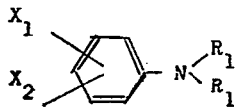

Formula V is usually formed as a by-product.

This latter compound is somewhat difficult and expensive to separate from the desired amine. The disubstituted amine of formula V cannot, however, form a chloroacyl anilide. Accordingly when the impure substituted aniline of Formula II is used in the process of the invention the disubstituted amine impurity is removed from the finished product by the water washing, when it forms a water soluble salt with the acidic products derived from the phosphoryl chloride. In the process of the present invention, the disubstituted amine neither interferes with the yield of the desired product nor with its purity. Accordingly there is no need to use a highly purified substituted amine of the general formula II in the present process. This is somewhat surprising as we find that the yield in the process described in British Patent Specification No. 1,316,782 is highly dependent on the purity of the amine used.

It is preferred that the chlorocarboxylic acid is charged to the reaction vessel in a slight excess over the substituted aniline. In general a 5 mole % excess is found to be sufficient.

Preferably an excess of phosphoryl chloride over that theoretically required to convert the chlorocarboxylic acid to this corresponding chloride is used. Whilst up to 100 mole % excess may be used, it is preferred that the excess is between 30 and 50 mole %.

The following Examples further illustrate the process of the present invention (Examples 2, 4, 6 and 8 are comparative examples).

EXAMPLE 1

Preparation of N-methyl chloro acetanilide from N-methyl aniline using phosphoryl chloride 76.75g (0.50 moles) of phosphoryl chloride and 107g (1.00 moles) of N-methyl aniline were added to 99.2g (1.05 moles) of monochloracetic acid. Alternate additions of 10% of the total amount of each of the N-methyl aniline and of the phosphoryl chloride were made with stirring at a temperature of 60° to 70°C over a period of 75 minutes. The reaction mixture was then stirred at 100° to 110°C for 4 hours, after which the reaction mixture was cooled to 70° to 80°C and then poured into warm water. The aqueous suspension was stirred vigorously whilst cooling until the product crystallised and then cooled further until the temperature reached 30° to 35°C. The precipitated crystalline product was separated from the aqueous phase by filtration and then washed with water. The washed product was dried in an oven at a temperature of 50° to 60°C. 157g of dry off-white crystals of N-methyl chloro acetanilide having a melting point of 69°C were obtained. The yield was 85.5% based on the theoretical yield from the N-methyl aniline in the starting material.

EXAMPLE 2

Comparative preparation of N-methyl chloro acetanilide from N-methyl aniline using phosphorus trichloride The preparation of Example 1 was repeated except that the addition of phosphoryl chloride was replaced by the addition of 68.75g (0.50 moles) of phosphorus trichloride. During the reaction at 100° to 110°C the reaction mixture became dark brown. 142.5g of a dry brown solid N-methyl chloro acetanilide having a melting point of 61°C were obtained. The yield was 77.6% based on the theoretical yield from the N-methyl aniline in the starting material.

EXAMPLE 3

Preparation of N-methyl chloro acetanilide from technical N-methyl aniline using phosphoryl chloride The preparation of example 1 was repeated except that 126g of a mixture containing 85.0% N-methyl aniline and 15.0% N,N dimethyl aniline was substituted for the 107g of N-methyl aniline. 170g of dry N-methyl chloro acetanilide having a melting point of 69°C were obtained. The yield was 92% of the theoretical yield based on the N-methyl aniline content of the total anilines in the starting material.

EXAMPLE 4

Comparative preparation of N-methyl chloro acetanilide from technical N-methyl aniline using phosphorus trichloride The comparative preparation of Example 2 was repeated except that 126g of a mixture containing 85.0% N-methyl aniline and 15.0% N,N dimethyl aniline was substituted for the 107g of N-methyl aniline. 123g of dry brown crystals of N-methyl chloro acetanilide having a melting point of 68°C was obtained. The yield was 67% of the theoretical yield based on the N-methyl aniline content of the total anilines in the starting material.

EXAMPLE 5

Preparation of N-methyl dichloro acetanilide from N-methyl aniline using phosphoryl chloride 76.75g (0.50 moles) of phosphoryl chloride and 107g (1.0 moles) of N-methyl aniline were added to 135.4g (1.05 moles) of dichloroacetic acid, in a manner similar to that used in Example 1. During the stirring of the reaction mixture at 100° to 110°C the mixture became brown in colour. 200g dry pink crystals of N-methyl dichloro acetanilide having a melting point of 64°C were obtained. The yield was 91.8% of the theoretical yield based on the N-methyl aniline in the starting material.

EXAMPLE 6

Comparative preparation of N-methyl dichloro acetanilide using N-methyl aniline and phosphorus trichloride The preparation of Example 5 was repeated except that the addition of phosphoryl chloride was replaced by the addition of 68.75g (0.50 moles) of phosphorus trichloride. During the stirring of the reaction mixture at 100° to 110°C a deep red-brown coloration developed and persisted. The filtered product was brown in colour and 180g of dry brown crystals of N-methyl dichloro acetanilide having a melting point of 67°C were obtained. The yield was 82.6% of the theoretical yield based on the N-methyl aniline in the starting material.

EXAMPLE 7

Preparation of N isopropyl chloro acetanilide from technical N isopropyl aniline using phosphoryl chloride 76.75g (0.50 moles) of phosphoryl chloride and 159g of technical N isopropyl aniline containing 85.1% by weight of N isopropyl aniline and 13.8% of N, N' diisopropyl aniline were added to 99.2g (1.05 moles) of monochloracetic acid. Alternate additions of 10% by weight of the total amount of each of the crude N isopropyl aniline and of the phosphoryl chloride were made with stirring at a temperature of 60° to 70°C over a period of 75 minutes. The reaction mixture was then stirred at 110°C for 4 hours, during which time the mixture remained light brown in colour. It was then cooled to 70° to 80°C and poured into warm water. The aqueous suspension was stirred vigorously whilst cooling until the product crystallised and then cooled further until the liquid temperature reached 30° to 35°C. The precipitated crystalline product was separated from the aqueous phase by filtration and was then washed with water. The washed product was then dried in an oven at a temperature of 50° to 60°C. 190g of dry off-white crystals of N isopropyl chloro acetanilide having a melting point of 76°C were obtained. The yield was 90% of the theoretical yield based on the N isopropyl aniline content of the total anilines in the starting material.

EXAMPLE 8

Comparative Preparation of N isopropyl chloro acetanilide from technical N isopropyl aniline using phosphorus trichloride The preparation of Example 7 was repeated except that the addition of phosphoryl chloride was replaced by the addition of 68.75g (0.50 moles) of phosphorus trichloride. During the stirring of the reaction mixture at 100° to 110°C a deep red coloration developed and persisted. The filtered product was red in colour and this reduced to a pink colour on washing. 137.5g of dry pink crystals of N isopropyl chloro acetanilide having a melting point of 76°C were obtained. The yield was 65% of the theoretical yield based on the N isopropyl aniline content of the total anilines in the starting material.

We claim:

1. A process for the preparation of substituted chloroacylanilides of the general formula:

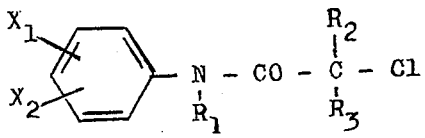

wherein $R_1$ is a group selected from alkyl groups having from 1 to 4 carbon atoms and a phenyl group; $R_2$ is an atom selected from the group consisting of a hydrogen atom and halogen atoms; $R_3$ is selected from the group consisting a hydrogen atom and alkyl groups having from 1 to 4 carbon atoms, and $X_1$ and $X_2$ are independently selected from the group consisting of a hydrogen atom, a halogen atom, a methyl group and an ethyl group, which process comprises acylating a substituted aniline of the general formula:

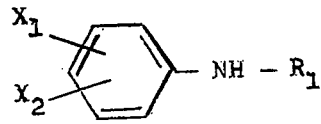

wherein $R_1$, $X_1$ and $X_2$ are as above defined, in the presence of phosphoryl chloride under substantially anhydrous conditions with a chlorocarboxylic acid of the general formula:

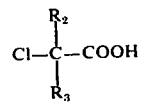

wherein $R_2$ and $R_3$ are as above defined.

2. A process as claimed in claim 1 wherein the substituted aniline of Formula II is selected from the group consisting of N-methyl aniline and N-isopropyl aniline.

3. A process as claimed in claim 1 wherein the carboxylic acid of Formula III is selected from the group consisting of chloroacetic acid, dichloroacetic acid, α-chloropropionic acid and α-chlorobutyric acid.

4. A process as claimed in claim 1 wherein the process is carried out at a temperature of from 40° to 160°C.

5. A process as claimed in claim 4 wherein the process is carried out at a temperature of from 60° to 120°C.

6. A process as claimed in claim 1 wherein the chloroacylanilide product of the process is purified by pouring the reaction mixture into water which is at a temperature above the melting point of the product, cooling sufficiently to allow the product to crystallise and further cooling to a temperature of from 30° to 35°C.

7. A process as claimed in claim 1 wherein the chlorocarboxylic acid is present in about a 5 mole % excess over the substituted aniline.

8. A process as claimed in claim 1 wherein from 30 to 50 mole % more phosphoryl chloride is present than is theoretically required to convert all the chlorocarboxylic acid to the corresponding acid chloride.

9. A process as claimed in claim 1 wherein the substituted aniline contains N,N-dialkylanilines as impurities.

* * * * *